US010571904B2

(12) United States Patent
Magno et al.

(10) Patent No.: US 10,571,904 B2
(45) Date of Patent: Feb. 25, 2020

(54) METHOD AND SYSTEM FOR MONITORING A MEDICAL OR DENTAL DEVICE

(71) Applicant: W&H Sterilization S.r.l., Brusaporto (BG) (IT)

(72) Inventors: Marino Magno, Almenno San Salvatore (IT); Klaus Maier, Salzburg (AT)

(73) Assignee: W&H Sterilization S.r.l., Brusaporto (BG) (IT)

( * ) Notice: Subject to any disclaimer, the term of this patent is extended or adjusted under 35 U.S.C. 154(b) by 242 days.

(21) Appl. No.: 15/785,235

(22) Filed: Oct. 16, 2017

(65) Prior Publication Data
US 2018/0052454 A1 Feb. 22, 2018

Related U.S. Application Data

(63) Continuation of application No. PCT/EP2016/059582, filed on Apr. 29, 2016.

(30) Foreign Application Priority Data

Apr. 29, 2015 (EP) .................................... 15165547

(51) Int. Cl.
*G05B 23/02* (2006.01)
*A61C 1/00* (2006.01)
*A61C 19/00* (2006.01)

(52) U.S. Cl.
CPC ........ *G05B 23/0283* (2013.01); *A61C 1/0007* (2013.01); *A61C 19/002* (2013.01)

(58) Field of Classification Search
CPC ........................... A61C 19/002; A61C 1/0007; G05B 23/0283; G08B 23/00
USPC ......... 702/127, 181, 182, 183, 184; 340/540
See application file for complete search history.

(56) References Cited

U.S. PATENT DOCUMENTS

2004/0236610 A1 11/2004 Nagaoka et al.
2011/0256496 A1 10/2011 Arzanpour
2012/0330613 A1* 12/2012 Sillman .................. G16H 40/40
702/184

(Continued)

FOREIGN PATENT DOCUMENTS

JP 2000330627 11/2000
JP 2005205193 8/2005

(Continued)

OTHER PUBLICATIONS

International Search Report for PCT/EP2016/059582, dated Jul. 5, 2016.

*Primary Examiner* — John H Le
(74) *Attorney, Agent, or Firm* — Klarquist Sparkman, LLP

(57) ABSTRACT

There is described a method and a system for monitoring a medical, in particular dental, device comprising at least two components, wherein at least one process parameter of the medical device which is sensitive to the functioning of the at least two components, is measured and stored for a plurality of operation cycles of the medical device and a maintenance requirement is recorded, when the process parameter reaches at least one preset and/or over a plurality of operation cycles calculated reference value, wherein a control unit assigns a maintenance requirement to one of the at least two components based on probabilistic evaluation of the recorded process parameters.

20 Claims, 2 Drawing Sheets

(56) References Cited

U.S. PATENT DOCUMENTS

2013/0264369 A1* 10/2013 Whitman ............ G06Q 10/087
                                                         227/175.1
2014/0266713 A1    9/2014 Sehgal et al.

FOREIGN PATENT DOCUMENTS

| JP | 5530020 | 6/2014 |
| WO | WO2014/154327 | 10/2014 |

* cited by examiner

METHOD AND SYSTEM FOR MONITORING A MEDICAL OR DENTAL DEVICE

CROSS REFERENCE TO RELATED APPLICATION

This application is a U.S. bypass continuation application of International Application No. PCT/EP2016/059582, filed Apr. 29, 2016, which in turn claims priority from European Patent Application No. 15165547.9, filed Apr. 29, 2015, now abandoned, which are incorporated herein by reference.

BACKGROUND

Field

The present invention relates to a method and system for monitoring a medical, in particular dental, device.

Description of Prior Art

The patent application WO 2014/54327 A1 describes a method for monitoring a reprocessing device, in particular a cleaning and/or disinfection device. According to the method one or more process parameters and the time of each reprocessing operation are logged over a plurality of reprocessing operations and are stored in association with the respective reprocessing operation. A trend analysis over at least one logged process parameter is carried out to determine whether the parameters follow a trend to a failure of the reprocessing device.

The advantage of this method for monitoring a reprocessing device, in particular a cleaning and; or disinfection device, is that a maintenance requirement of a medical device can be detected based on the monitoring of the process parameters. This enables to avoid a failure or a breakdown of the medical device.

SUMMARY

It would be advantageous to provide a method for monitoring a medical, in particular dental, device, which provides more detailed information about the maintenance requirement of the medical device than a general maintenance requirement, as proposed in the prior art.

According to one embodiment, this is accomplished by a method for monitoring a medical, in particular dental, device comprising at least two components, wherein at least one process or operation parameter of the medical device, which is sensitive to the functioning of the at least two components, is measured and stored for a plurality of operation cycles of the medical device and a maintenance requirement is recorded, when the operation or process parameter reaches at least one preset and/or over a plurality of operation cycles calculated reference value, wherein a control unit assigns a maintenance requirement to one of the at least two components based on probabilistic evaluation of the recorded operation or process parameters.

By providing a method for monitoring a medical, in particular dental, device, wherein a control unit for the medical device carries out probabilistic evaluation of the recorded process parameters, it is possible to assign, in particular classify, a maintenance requirement to one specific component of the medical device. The medical device thus does not have to be checked on the whole, as is known in the prior art, but instead only one or several specific identified components have to be reviewed in view of functioning, repairing or renewing. Thus according to the especially preferred embodiment of the invention, the quantities of resources required for manually identifying the technical defect, in particular the component with the technical defect, are substantially reduced in this way and at the same time the duration of maintenance is shortened.

The medical, in particular dental, device monitored and described herein is understood to refer in particular to cleaning, disinfection, care and/or sterilization devices, which execute or enable a cleaning treatment, in particular with water, steam, compressed air and/or a cleaning agent, a disinfection treatment, such as thermal disinfection, a care treatment by introducing a lubricant, such as oil, and/or a sterilization treatment, in particular by steam.

Further, the medical, in particular dental, device monitored and described herein is understood to refer in particular to medical, in particular, dental units to drive medical instruments and to the medical instruments themselves. The medical, in particular dental, instruments have a drive mechanism or a supply line for the drive mechanism and are preferably designed as medical handpieces or contra-angle handpieces having a first connecting device for connecting the medical, in particular dental, instruments, which preferably serve to process hard or soft tissue or for inserting implants. By a second connection device, the medical instruments can be connected to the medical, in particular dental, units, motors or media sources. The dental units supply the working media required for the medical instruments, for example spray air and/or spray water for cooling, instrument-related data, and/or electric energy for supplying electric components, sensors or electric memories.

So, the medical device monitored and described herein is understood to refer to all the medical devices, which comprise multiple technical components, whose functioning have to be monitored.

The monitored components of the medical, in particular dental, device are preferably at least a mechanical, in particular machine, component, such as a pump, a steam generator, a condenser, a heating element, a filter, an electric motor, a sealing element, a sensor, a compressor, a valve, a bearing, an operating element, such as a switch or a display, and/or a supply element, such as energy supply units, for example accumulators.

The process parameters measured and stored for a plurality of operation cycles of the medical device, in particular as function of time, are preferably one of: a temperature value, a pressure value, a quantity of material, a moisture value, an electrical conductivity value, an operation time, an electric energy value, a light intensity value.

The term process parameters, which are sensitive to the functioning of the components of the medical device refers to process and operation parameters, which depend on the operation of these components of the medical device. For example, a temperature in a sterilization chamber of a steam sterilizer depends on the operation of a heating element and a media pump of a media supply, which introduces steam into the sterilization chamber to heat the chamber. So a technical defect of the heating element or of the media pump can be detected based on monitoring of the chamber temperature.

During probabilistic evaluation, in particular to assign a maintenance requirement to components of the medical device, the recorded parameters are measured and stored for a plurality of operation cycles of the medical device. The parameters are then applied to a classifier. The classifier is a program executable on said control unit of the medial device. The classifier is able to produce an output calculation, in particular a probability distribution, over the set of technical components of the medical device. The maintenance requirement is recorded and assigned to the component of the medical device with the highest probability.

According to a first exemplary embodiment of the method for monitoring a medical, in particular dental, device with at least two components, multiple process parameters of the medical device are measured for a plurality of operation cycles of the medical device and at least one performance value is created and stored for each operation cycle of the medical device based on the monitored process parameters. The control unit of the medical device, which is integrated or connected to the medical device by a wired or wireless connection, assigns the maintenance requirement to one of the components based on probabilistic evaluation of the performance value.

According to a third exemplary embodiment of the method for monitoring a medical, in particular dental, device, the control unit modifies the operation cycle of the medical device depending on the component with the assigned maintenance requirement. So a failure or a breakdown of the medical, in particular dental, device can be avoided.

Alternatively or in addition to the aforementioned method, the control unit indicates the component with the assigned maintenance requirement and/or indicates service instructions for the component with the assigned maintenance requirement. The maintenance requirement and the service instructions are in particular indicated by visual or audible signals.

According to a fourth exemplary embodiment of the method fir monitoring a medical, in particular dental, device, the maintenance requirement and the service instructions are transmitted from the control unit to a remote evaluation unit. In turn, the evaluation unit preferably transmits indication, service or operation commands for the medical device to the control unit.

A medical, in particular dental, device with at least two components comprises a control unit to measure and store at least one process parameter of the medical device, wherein the control unit comprises means, in particular a computer program executable on a processor of said control unit, for processing the method for monitoring a medical, in particular dental, device as previously described.

According to a first exemplary embodiment of the medical, in particular dental, device, the control unit is integrated in the medical device. Alternatively, the control unit can be connected to the medical device by a wired or wireless connection between the medical device and the control unit. In this case the control unit is positioned in a separate housing and connect to the medical device via a cable or a wireless connection, which is preferably based on radio communication.

Alternatively or in addition to the aforementioned embodiment of the medical, in particular dental, device, the control unit is connected to a remote evaluation unit, in particular to a computer or server by a wired connection, for example a network, or a wireless connection, specifically by a wireless local area network (WLAN).

In addition, according to a second exemplary embodiment of the medical, in particular dental, device, the control unit and the evaluation unit comprise bidirectional communication means to transmit data and/or signals between the control unit and the evaluation unit.

According to the previously described embodiments, the medical, in particular dental, device is in particular one of: dental treatment unit, handpiece, motor, autoclave, maintenance device.

The present method and system for monitoring a medical, in particular dental, device is characterized by the following advantages:

As mentioned before, through probabilistic evaluation of the recorded process parameters, it is possible to assign, in particular classify, a maintenance requirement to one or several components of the medical device with high accuracy. This is one advantage of the invention. Only the identified components have to be reviewed in view of functioning, repaired or renewed. This permits checking the whole medical device. The maintenance time is drastically shortened.

Another advantage consists of the fact that at least one performance value is created and stored for each operation cycle of the medical device based on the monitored process parameters and the control unit of the medical device assigns the maintenance requirement to one of the components based on probabilistic evaluation of the performance value. Thus according to one of the especially preferred embodiments of the invention, the quantities of data, in particular process parameter values, stored and processed are substantially reduced in this way. Thus storage space and costs can be drastically reduced. At the same time transmission and evaluation time is shortened.

These and other embodiments will be described below with reference to the following drawings.

DETAILED DESCRIPTION

Figure 1:
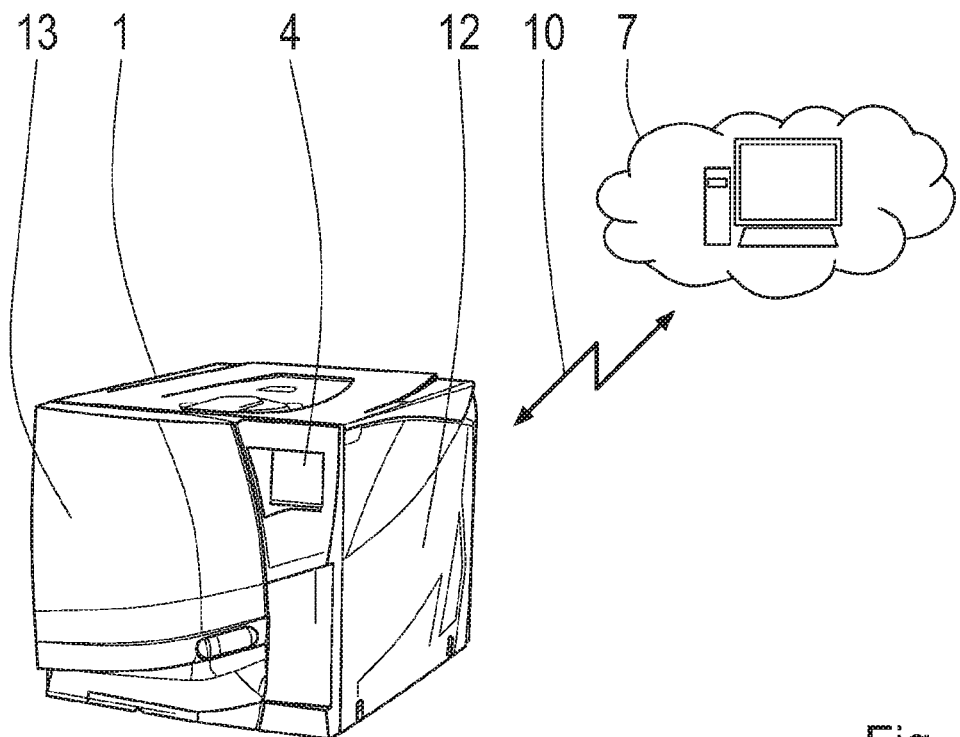
FIG. 1 shows a first exemplary embodiment of a medical device, in particular of a sterilization device, comprising an internal control unit with means for processing the proposed method for monitoring the medical, in particular, dental device and a remote evaluation unit.

FIG. 1 diagrammatically shows a sterilization device 1 for medical, in particular dental, instruments. The sterilization device 1 comprises a housing 12 in which a sterilization chamber is arranged. The chamber is defined by a casing and an air-tight door 13. Specifically to withstand pressure differences between the inside of the chamber and outside, the chamber and the door 13 are preferably made of stainless steel. The chamber comprises several inlet and outlet openings, which are connected to a media supply for feeding and/or discharging media, such as steam, air and so on.

The media supply may comprise in particular, among other things, a certain number of channels to convey the above mentioned media, containers for the sterilization agents or waste water, connections to fluid sources, in particular to a air or water sources, and components, such as heating elements, condenser, fluid or evacuation pumps, filter and so on. Furthermore, the media supply comprises actuators, for example valves, sensors, such as temperature, pressure, conductivity, flow or concentration sensors.

In addition to the media supply, the sterilization device 1 comprises a control unit 4, which is arranged in the sterilization device 1 to control and/or regulate a sterilization process. The control unit 4 preferably comprises a processor, a memory unit, a display, a control panel for the user, a communication interface, and a connection to a power source, to the above mentioned technical components, to the several sensors of the media supply and to additional sensors, which are arranged in or are connect to the sterilization chamber and/or to the technical components to monitor the operation of the sterilization device 1.

The control unit 4 comprises means, in particular a computer program with a probabilistic classifier executable on the processor of said control unit 4, to process the method for monitoring the functioning of the sterilizer 1 as mentioned above. Preferably, two process parameters, such as the temperature and the pressure in the chamber, which are sensitive to the functioning of the components of the sterilizer 1, are measured and stored for a plurality of operation cycles of the sterilizer. A maintenance requirement is recorded, when the process parameter reaches at least one preset and/or over a plurality of operation cycles calculated reference value. The classifier of the control unit 4 calculates a probability distribution over the set of technical components of the medical device and assigns a maintenance requirement to one of the components of the sterilizer 4, such as the heating element, condenser, fluid or evacuation pump, or filter based on probabilistic evaluation of the recorded process parameters. Especially, the control unit 4 creates and stores for each operation cycle of the sterilizer 4 one performance value based on the monitored process parameters and assigns the maintenance requirement to one of the components based on probabilistic evaluation of the performance value.

According to the first embodiment, the assigned maintenance requirement and the component is indicated directly on the sterilizer by the display of the control unit 4. The assigned maintenance requirement is preferably one of: door sealing defect, heating pump fail, condenser broken, sensors damaged and so on. In addition, the control unit preferably displays service instructions, such as "change filter" or "replace door sealing" for the component with the assigned maintenance requirement by visual and/or audible signals.

Furthermore, the communication interface of the control unit 4 serves to transmit the maintenance requirements and the service instructions from the control unit 4, in particular from the sterilization device 1, to a remote evaluation unit 7, in particular to a server, wherein the server transmits indication, service or operation commands for the sterilizer 1 to the control unit 4. In this embodiment, the data and/or signals are transmitted between the control unit 4 and the evaluation unit 7 by a wireless data transmission 10 (e.g., via radiofrequency, infrared, inductive or capacitive data transmissions). The medical device 1 according to the first embodiment comprises bidirectional communication means 10.

Figure 2:
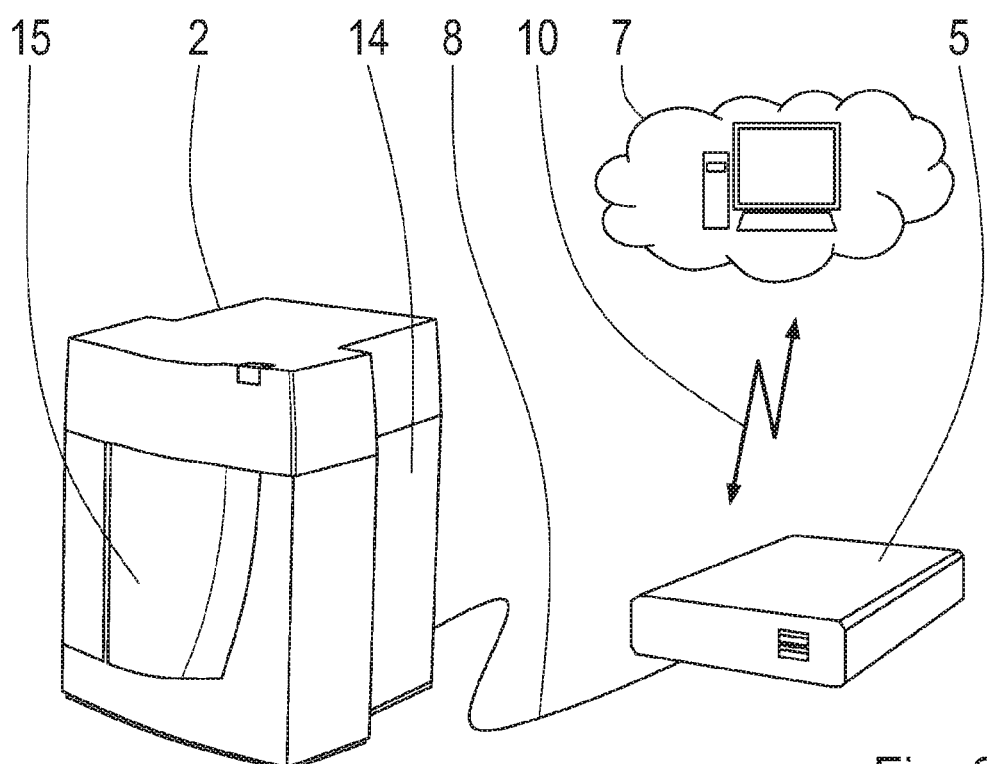
FIG. 2 shows a second embodiment of medical device, in particular for cleaning, disinfection, care and/or sterilization, comprising an external control unit and a remote evaluation unit.

FIG. 2 shows a medical device, in particular a cleaning, disinfection, care and/or sterilization device 2, which comprises a housing 14, preferably made of plastic, with a door 15, which closes a maintenance chamber arranged inside of the housing 14. Several connection ports for medical, in particular dental, instruments are provided in the chamber. Through the ports cleaning, disinfection, sterilization and care agents can be transported into the interior of the medical instruments based on a media supply as mentioned in FIG. 1. Additionally, through nozzles, which are arranged in the maintenance chamber, the cleaning, disinfection, sterilization and care agents can be spread onto the outside of the medical instruments.

An external control unit 5, which comprises means to process the method for monitoring the functioning of the medical device 2, as mentioned above, is connected to the medical device 2. The control unit 5 is connected in this embodiment to the medical device 2 by a wired connection 8, preferably via a cable 8. As mentioned before, the control unit 5 is connected to a remote evaluation unit 7 by the wireless connection 10.

According to this further embodiment, the control unit 5 comprises means to modify the operation cycle of the medical device 2 depending on the component with the assigned maintenance requirement. For example, when the control unit 5 assigns the maintenance requirement to the vacuum pump based on probabilistic evaluation of the recorded process parameters, the control unit 5 modifies one or more operation parameters of the pump, for example an evacuation time to compensate a detected limitation of the pump capacity. Additionally, according to this embodiment the control unit 5 transmits the monitored maintenance requirement to the remote evaluation unit 7, in particular to a server of a service center for the medical device 2. So the service center can send a technician to repair or change the monitored component of the medical device 2 with the detected technical defect.

Figure 3:
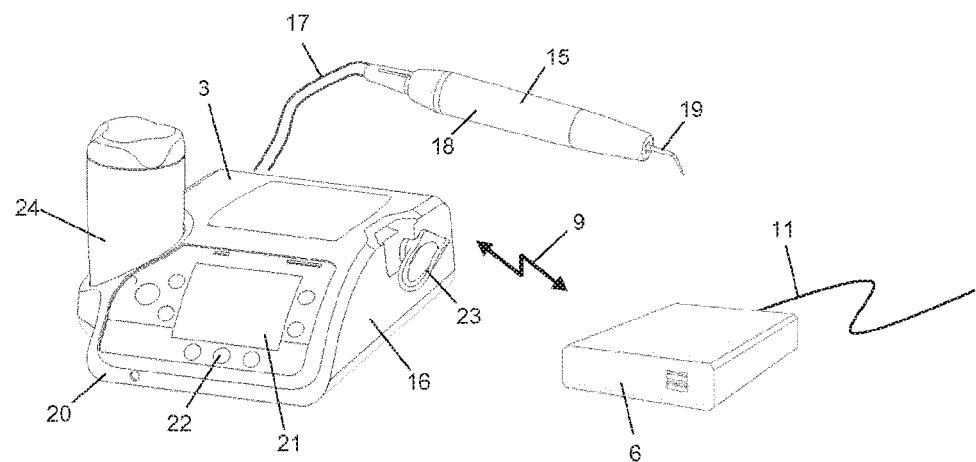
FIG. 3 shows a third embodiment of medical device, in particular a dental treatment unit, comprising a control unit with means for processing the proposed method for monitoring the medical, in particular, dental device.

FIG. 3 shows a further preferred embodiment of the monitored medical device 3 using the proposed method. The medical device 3 as shown in FIG. 3 is a dental scaler treatment unit 3. The dental treatment unit 3 comprises a handpiece 15, a control device 16 and a connection tube 17, which connects the handpiece 15 with the control device 16. The handpiece 15 has a hand grip 18, in which a drive unit for a treatment tool 19, a tool receptacle, and an illumination device are arranged. The control device 16 has a housing 20 with a display 21, at least one adjusting element 22, such as pushbutton, for selecting or changing operating parameters, a handpiece rest 23 and a liquid source 24 with a cooling or rinsing liquid. The tube 17 contains multiple media lines, in particular fluid and electric lines. The fluid lines connects the liquid source 24 to the tool receptacle. So liquid can be dispensed via an opening in the handpiece to the treatment area and/or to the tool. The electric lines connect the drive unit in the handpiece 15 to the control device 16, in particular to a power source. The drive unit preferably comprises a piezoelectric vibration generator with a sonotrode connected to the vibration generator and designed as a hollow oscillating shaft. At one end of the sonotrode the tool receptacle is provided. The media line opens into the hollow sonotrode from which the liquid is transferred to the tool receptacle. The illumination device comprises a circuit board and at least one semiconductor element, in particular a light-emitting diode.

According to this embodiment, a external control unit 6 comprises means to process the method for monitoring a medical device as mentioned above. At least one process parameter, which is sensitive to the functioning of the components of the dental scaler treatment unit 3, such as the vibration response of the sonotrode, which depends on the functioning of a vibration generator and a media pump, which conducts fluid through the hollow sonotrode, is measured and stored for a plurality of operation cycles of the dental treatment unit 3. A maintenance requirement is recorded, when the process parameter reaches at least one preset and/or over a plurality of operation cycles calculated reference value. And the control unit 6 assigns a maintenance requirement to one of the at least two components, in particular to the media pump or to the vibration generator, based on probabilistic evaluation of the recorded process parameters.

In this embodiment, the external control unit 6 is connected to dental treatment unit 3 by a wireless connection 9. In addition, the control unit 6 is connectable to additional medical devices, such as cleaning, disinfection, care and/or sterilization devices and designed to monitor these medical devices simultaneously using the proposed method. The control unit 6 indicates the component with the assigned maintenance requirement and/or the service instructions directly on the medical devices using for example the display 21 of the dental scaler treatment unit 3.

Within the scope of the present invention it is self-evident that the inventive method and system for monitoring a medical, in particular dental, device according to the invention is not limited to the exemplary embodiments described here, but instead includes all embodiments which apply or include fundamentally analogous function principles. In addition, all the features of all the embodiments described and depicted here may be combined with one another.

What is claimed is:

1. A method for monitoring a medical or dental device comprising at least two components, comprising:
   measuring at least one process parameter of the medical or dental device which is indicative of the functioning of the at least two components for a plurality of operation cycles of the medical device,
   storing the at least one process parameter for each of the plurality of operation cycles;
   determining if a maintenance requirement is triggered by comparing if the at least one process parameter has reached at least one reference value, wherein the reference value is preset and/or calculated over multiple operation cycles,
   using a control unit to probabilistically evaluate the maintenance requirement relative to the stored at least one process parameter for the at least two components; and
   assigning the maintenance requirement to one of the at least two components based on a result of the probabilistic evaluation of the stored at least one process parameter.

2. The method for monitoring a medical or dental device according to claim 1, wherein measuring at least one process parameter of the medical or dental device comprises measuring multiple process parameters, further comprising calculating at least one performance value for each operation cycle of the medical device based on the process parameters and storing the at least one performance value, wherein using the control unit to probabilistically evaluate the maintenance requirement comprises using the performance value and the control unit assigns the maintenance requirement to one of the components based on probabilistic evaluation of the performance value.

3. The method for monitoring a medical or dental device according to claim 1, wherein the components of the medical or dental device comprises at least one of: a mechanical component, a pump, a steam generator, a condenser, a heating element, a filter, an electric motor, a sealing element, a sensor, a compressor, a valve, a bearing, an operating element, a switch, a display, a supply element, or an energy supply unit.

4. The method for monitoring a medical or dental device according to claim 1, wherein at least one of a temperature value, pressure value, a quantity of material, a moisture value, an electrical conductivity value, an operation time, an electric energy value, or a light intensity value is measured and stored as one of the process parameters during operation of the medical or dental device.

5. The method for monitoring a medical or dental device according to claim 1, further comprising using the control unit to modify an operation cycle of the medical or dental device depending on the component to which the maintenance requirement is assigned.

6. The method for monitoring a medical or dental device according to claim 1, wherein the control unit communicates an indication of at least one of an identification of the component with the assigned maintenance requirement or service instructions for the component with the assigned maintenance requirement.

7. The method for monitoring a medical or dental device according to claim 6, wherein the maintenance requirement or the service instructions are indicated by visual or audible signals.

8. The method for monitoring a medical or dental device according to claim 6, further comprising transmitting the maintenance requirement or the service instructions from the control unit to a remote evaluation unit.

9. The method for monitoring a medical or dental device according to claim 8, further comprising transmitting an indication, service instructions or an operation command for the medical device from the remote evaluation unit to the control unit.

10. A medical or dental device with at least two components and comprising a control unit to measure and store at least one process parameter of the medical device for a plurality of operation cycles of the medical or dental device, wherein the control unit is configured to process a method for monitoring the medical or dental device, the method comprising:
    measuring and storing at least one process parameter of the medical device which is sensitive to the functioning of the at least two components for a plurality of operation cycles of the medical or dental device,
    recording a maintenance requirement when the process parameter reaches at least one reference value which is preset and/or calculated over a plurality of operation cycles, and
    assigning a maintenance requirement to one of the at least two components based on probabilistic evaluation of the recorded process parameters by the control unit.

11. The medical or dental device according to claim 10, wherein the control unit is integrated in or connected to the medical or dental device by a wired or wireless connection between the medical or dental device and the control unit.

12. The medical or dental device according to claim 10, wherein the control unit is connected to a remote evaluation unit by a wired or wireless connection.

13. The medical or dental device according to claim 12, wherein the control unit and the evaluation unit comprise bidirectional communication means to transmit data and/or signals between the control unit and the evaluation unit.

14. The medical or dental device according to claim 10, wherein the medical or dental device comprises at least one of a dental treatment unit, an instrument, a motor, a cleaning device, a disinfection device, a handle element, a maintenance device or a reprocessing device.

15. The method for monitoring a medical or dental device according to claim 1, wherein the at least one process parameter is measured and stored for a plurality of operation cycles as a function of time.

16. The method for monitoring a medical or dental device according to claim 1, wherein based on the probabilistic evaluation of the at least one measured and stored process parameter, an output calculation over the at least two components of the medical or dental device is output to assign the maintenance requirement to one of the at least two components.

17. The method for monitoring a medical or dental device according to claim 16, wherein the output calculation comprises a probability distribution.

18. The method for monitoring a medical or dental device according to claim 1, wherein the probabilistic evaluation of the at least one measured and stored process parameter is performed by a computer program executable on a processor of the control unit.

19. The method for monitoring a medical or dental device according to claim 1, wherein determining if a maintenance requirement is triggered comprises comparing if a value or parameter which is based on or derived from the at least one process parameter has reached at least one reference value.

20. A method for monitoring a medical or dental device comprising at least two components, comprising:
measuring during an operation cycle of the medical device a plurality of values of a plurality of different process parameters of the medical or dental device wherein the values of at least two different process parameters of the plurality of different process parameters are indicative of the functioning of each of the at least two components,
calculating at least one performance value of the medical device based on the values of the at least two different process parameters indicative of the functioning of each of the at least two components and storing the at least one performance value;
determining if a maintenance requirement is triggered by comparing if the at least one performance value has reached at least one reference value, wherein the reference value is at least one of preset and calculated over multiple operation cycles,
using a control unit to probabilistically evaluate the maintenance requirement for the at least two components based on the performance value; and
assigning the maintenance requirement to one of the at least two components based on a result of the probabilistic evaluation of the performance value by the control unit.

* * * * *